US006214771B1

(12) United States Patent
Dexter

(10) Patent No.: US 6,214,771 B1
(45) Date of Patent: *Apr. 10, 2001

(54) AQUEOUS SPRAY COMPOSITIONS

(75) Inventor: Robin W. Dexter, Yardley, PA (US)

(73) Assignees: American Cyanamid Company; Five Giralda Farms, both of Madison, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/744,716

(22) Filed: Oct. 29, 1996

Related U.S. Application Data

(60) Provisional application No. 60/007,272, filed on Nov. 6, 1995.

(51) Int. Cl.$^7$ .............................. A01N 63/00; C09K 3/30
(52) U.S. Cl. ...................... 504/360; 504/363; 514/772.3; 516/7; 516/6; 71/64.13
(58) Field of Search .............................. 252/305, 315.4; 516/6, 7; 71/DIG. 1, 64.13; 504/116, 360, 363; 514/772.3

(56) References Cited

U.S. PATENT DOCUMENTS

| | | | |
|---|---|---|---|
| 3,175,898 | * | 3/1965 | Seymour et al. ............... 71/DIG. 1 |
| 3,360,356 | * | 12/1967 | Vartiak ............................. 504/187 |
| 3,764,293 | * | 10/1973 | Durward ....................... 71/DIG. 1 |
| 3,934,005 | * | 1/1976 | Albert ................................. 514/477 |
| 4,447,413 | * | 5/1984 | Rippstein, Jr. ................. 514/772.7 |
| 4,505,827 | | 3/1985 | Rose et al. ............................. 252/1 |
| 4,510,081 | * | 4/1985 | Bronner et al. ..................... 252/603 |
| 4,610,311 | * | 9/1986 | Bronner et al. ..................... 252/603 |
| 4,770,814 | | 9/1988 | Rose et al. ....................... 252/315.4 |
| 4,787,928 | | 11/1988 | Balassa ................................. 71/23 |
| 4,880,565 | | 11/1989 | Rose et al. ........................... 252/1 |
| 5,415,877 | | 5/1995 | Winston ............................. 424/717 |
| 5,424,270 | * | 6/1995 | Winston ............................. 504/101 |
| 5,432,146 | * | 7/1995 | Winston ............................. 504/101 |
| 5,529,975 | * | 6/1996 | Chamberlain ....................... 504/116 |

FOREIGN PATENT DOCUMENTS

| | | | |
|---|---|---|---|
| 1209361 | 8/1986 | (CA) | ....................................... 71/41 |
| 0 055 857 | * 7/1982 | (EP) . | |
| 107009 | 5/1984 | (EP) | .............................. A01N/25/04 |
| 0 245 970 | * 11/1987 | (EP) . | |
| 2107986 | 5/1983 | (GB) | .............................. A01N/25/00 |
| WO 95/8389 | 3/1995 | (WO) | .............................. B01F/17/00 |
| WO 96/9761 | 4/1996 | (WO) | .............................. A01N/25/30 |

OTHER PUBLICATIONS

McCutcheon's Volume 1: Emulsifiers & Detergents North American Edition, (McCutcheon Division, MC Publishing Co., Glen Rock, NJ, copyright 1993) pp. 48, 139, 177, 193, & 206, Jan. 1994.*

Whistler, Industrial Gums, second edition (Acedemic Press, NY, NY Copyright 1973) pp. 704–705, Nov. 1973.*
R.W. Dexter, "Measurement of Extensional Viscosity of Polymer Solutions and its Effects on Atomization from a Spray Nozzle", Atomization and Sprays 6 167–191 (1996). Month unknown.
Haq, K., Akesson, N.B. and Yates W.E., "Analysis of Droplet Spectra and Spray Recovery as a Function of Atomizer Type and Fluid Physical Properties," Pesticide Formulations and Application Systems: Third Symposium, ASTM STP 828, T.M. Kameko and N.B. Akesson, Eds., American Society for Testing and Materials, Philadelphia, 1983, Month unknown pp. 67–82.
Goddard, E.D., 1986, Month unavailable "Polymer–surfactant interaction. Part 1. Uncharged water–soluble polymers and charged surfactants", *Colloids and Surfactants,* 19, 255.
Jones, M.N., 1966, Month unavailable "The interation of sodium dodecyl sulfate with polyethylene oxide", *Journal of Colloid and Interface Science,* 23, 36–42.
Cabane, B. and Duplessix, R., 1982, Month unavailable "Organization of surfactant micelles adsorbed on a polymer molecule in water: a neutron scattering study", *J.Phys. (Paris),* 43.
Mansour, A. and Chigier, 1994, Month unavailable "Atomization of non–Newtonian liquids", *ICLASS–94 Rouen, France,* Paper 1–28, 213.
Bouse, L.F. Carlton, J.B. and Jank, P.C., 1988, Month unavailable "Effect of water–soluble polymers on spray droplet size", *Transactions of the ASAE,* 31, (6), 1633–1641.
Cabane, B., 1977, Month unavailable "Structure of some polymer–detergent aggregates in water", *J. Physical Chem,* 81 No. 17, pp. 1639.
Hewitt, A.J., et al, 1993, Month unavailable, "Effect of adjuvants and formulations on aetial spray drift potential", *Pesticide Science,* 37, 209–211.
Okzan, H.E., et al, 1993, "Effects of drift retardant chemicals on spray drift, droplet size and spray pattern", *Pesticide Formulations and Application Systems: 13th Volume,* ASTM STP 1183, Paul D. Berger et al, Eds. ASTM, Philadelphia, 1993. Month unavailable.
Li. Y. and Dubin, P.L., 1994, Month unavailable "Polymer surfactant complexes", *Structure and flow in surfactant solutions,* ACS Symposium Series 578, Eds. Herb, C.A. amd Prud'homme, R.K., Chapter 23, 320–336.

* cited by examiner

*Primary Examiner*—Richard D. Lovering
*Assistant Examiner*—Daniel S. Metzmaier
(74) *Attorney, Agent, or Firm*—Charles F. Costello

(57) ABSTRACT

An aqueous spray composition comprising about 0.0001 to 1 wt/wt % of a water-soluble poly(ethylene oxide) having a molecular weight greater than about $5 \times 10^5$ Daltons and at least about 0.05 wt/wt % of a surfactant selected from the group consisting of a sulfonate surfactant and a sulfate surfactant. Said compositions exhibit reduced spray drift. Said compositions are employed in methods for increasing the median diameter of spray droplets and have utility in agricultural spray applications.

10 Claims, No Drawings

AQUEOUS SPRAY COMPOSITIONS

This application claims priority from co-pending provisional application Ser. No. 60/007,272 filed Nov. 6, 1995.

BACKGROUND OF THE INVENTION

Aqueous spray compositions have been used for several decades to apply agricultural compounds. However, the results obtained from aqueous spray compositions are not entirely satisfactory because spray drift may occur. Spray drift is especially undesirable because under/over application of agricultural compounds may occur. In addition, spray drift may contaminate non-target areas with unacceptable levels of agricultural compounds.

In recent years, the potential for drift from agricultural spray applications has become a matter of intensive study. One result of that study is the identification of spray droplet size as one of the most important factors contributing to drift. High molecular weight, water-soluble polymers are currently added to spray compositions to increase droplet size and thereby reduce drift. However, high molecular weight, water-soluble polymers are not entirely satisfactory because they are expensive to use at the concentrations required to substantially increase droplet size.

SUMMARY OF THE INVENTION

The present invention provides an aqueous spray composition comprising about 0.0005 to 1 wt/wt % of a water-soluble polymer and at least about 0.05 wt/wt % of a surfactant selected from the group consisting of a sulfonated surfactant, a sulfated surfactant and mixtures thereof, provided that the surfactant has at least one straight or branched carbon chain containing at least nine carbon atoms. Preferably, said polymer is selected from the group consisting of a poly(ethylene oxide), a poly(vinyl alcohol), a poly(vinyl pyrrolidone), a poly(vinyl ether), a cellulose ether, and mixtures thereof.

The present invention further provides a method for reducing the spray drift of an aqueous spray composition and a method for increasing the median diameter of spray droplets.

Advantageously, the present invention provides aqueous spray compositions which exhibit a reduced potential for spray drift when compared to spray compositions containing conventional spray drift control additives such as high molecular weight, water-soluble polymers. The aqueous spray compositions of the present invention preferably contain about 0.005 to 0.05 wt/wt % of the polymer, and about 0.05 to 1 wt/wt % of the surfactant.

It is, therefore, an object of the present invention to provide an aqueous spray composition having increased droplet size and exhibiting reduced spray drift potential.

It is another object of the present invention to provide a method for increasing the mean droplet diameter of an aqueous spray composition, and to reduce the spray drift potential thereof.

Other objects of the present invention will be apparent to those skilled in the art from the following disclosures.

DETAILED DESCRIPTION OF THE INVENTION

In one preferred embodiment of the present invention, from about 0.0005 to about 1 wt % of a water-soluble polymer and from about 0.05 to about 1 wt % of a sulfonated or sulfated surfactant are added to an aqueous spray composition containing an agricultural compound; e.g., a herbicide to form an aqueous spray composition of the present invention.

It has been found that the median diameters of spray droplets are dramatically increased when the polymer and surfactant of this invention are present in aqueous spray compositions. The larger droplets are less prone to spray drift.

The combination of surfactant and polymer in the present invention is important in providing significantly increased droplet size and reduced spray drift potential. The water-soluble polymer and surfactant of the present invention are believed to associate or complex with one another in the aqueous composition, promoting larger droplet sizes. These larger droplets tend to drift less when sprayed, allowing the composition to be more precisely applied where needed.

Generally, it has been found that at least about 0.05% surfactant and about 0.0005% polymer by weight are needed to provide the advantageous droplet size enhancement of the present invention. The precise amount required will vary depending on the other elements of the composition, the choice of polymer and the choice of surfactant. Increasing the percentage of the surfactant and/or polymer further increases droplet size. The exact percentages that are best for a given composition can readily be determined by one of skill in the art, and will be dependent on the desired median diameter of the spray droplet.

The optimum droplet size depends on the application for which the composition is used. If droplets are too large, there will be less coverage by the spray; i.e, large droplets will land in certain areas while areas inbetween will receive little or no spray composition. The maximum acceptable droplet size may depend on the amount of composition being applied per unit area and the need for uniformity in spray coverage. Smaller droplets provide more even coverage, but are more prone to drift during spraying. If it is particularly windy during spraying, larger droplets may be preferred, whereas on a calmer day smaller droplets may be preferred.

The spray droplet size may also depend on the spray apparatus; e.g., nozzle size and configuration. One skilled in the art will readily be able to adjust the percentage of surfactant and/or polymer in the composition to provide the desired droplet size for a given apparatus, application, and conditions.

Preferred polymers of the present invention include poly(ethylene oxide) polymers, poly(vinyl alcohol) polymers, poly(vinyl pyrrolidone) polymers, poly(vinyl ether) polymers, and cellulose ether polymers all having molecular weights greater than about $2 \times 10^5$ Daltons. Poly(ethylene oxide) polymers having a molecular weight of greater than about $5 \times 10^5$ Daltons are more preferred with poly(ethylene oxide) polymers having a molecular weight of about $1 \times 10^6$ to $1 \times 10^7$ Daltons being most preferred.

The surfactant is an especially important element of the present invention and is present in at least about 0.05 wt/wt %. Surfactants suitable for use in the present invention include α-olefin sulfonates, alkylaryl sulfonic acids and salts, alkyl sulfates, α-olefin sulfates, ethoxylated alcohol sulfates, and ethoxylated alkylphenol sulfates, all having at least one straight or branched carbon chain containing at least nine carbon atoms. The carbon chain length is important to promote increased droplet size and reduced spray drift potential.

Surfactants which are preferred for use in this invention include α-$(C_9$–$C_{18})$olefin sulfonates such as an α-$(C_{14}$–$C_{16})$ olefin sulfonate, $C_9$–$C_{18}$alkylbenzene sulfonic acids and salts such as dodecylbenzene sulfonic acid, sodium dodecyl benzene sulfonate and triethanolamine dodecyl benzene sulfonate, $C_9$–$C_{18}$ alkyl sulfates such as sodium decyl sulfate and sodium dodecyl sulfate, α-($C_9$–$C_{18}$)olefin sulfates such as an α-($C_{14}$–$C_{16}$)olefin sulfate, ethoxylated $C_9$–$C_{18}$ alcohol sulfates such as sodium dodecyl alcohol (ethoxylate-3) sulfate and sodium tridecyl alcohol(ethoxylate-3) sulfate, and ethoxylated $C_9$–$C_{18}$ alkylphenol sulfates such as an ethoxylated nonylphenol sulfate.

The compositions of the present invention are useful for the application of agricultural compounds such as pesticides, plant growth regulators, safeners, and mixtures thereof. In particular, the compositions of this invention are especially useful for the application of pesticides such as herbicides, insecticides, fungicides, nematicides, and molluscicides. In general, the agricultural compound is present in the spray compositions of this invention in an amount up to about 50 wt/wt % and is preferably present in an amount from about 0.001 to 50 wt/wt %. The amount of agricultural compound present in the compositions of this invention will depend on a variety of factors such as spray volume, application rate and application mode (for example, aerial vs. tractor application).

The present invention also provides a method for increasing the median diameter of spray droplets and reducing the spray drift of an aqueous spray composition which comprises adding to the composition about 0.0005 to 1 wt/wt % of a polymer of this invention and at least about 0.05 wt/wt % of a surfactant of this invention. Advantageously, the polymer and surfactant may be added to the composition in the field prior to spraying or, in the case of a ready to use composition, may be added during the manufacture of the composition.

In one embodiment the aqueous spray compositions of this invention containing an agricultural compound may be prepared by mixing together (1) a concentrate composition containing the agricultural compound, (2) a sufficient amount of the polymer, (3) a sufficient amount of the surfactant, and (4) water. Additional additives such as antifoam agents, dyes, preservatives and the like may be added to the spray compositions of the present invention.

In order to facilitate a further understanding of the invention, the following example is presented primarily for the purpose of illustrating more specific details thereof. The invention should not be deemed limited thereby except as defined in the claims.

EXAMPLE 1

Evaluation of median droplet diameter of various poly(ethylene oxide)/surfactant compositions Aqueous spray compositions are prepared by dissolving 0.15 wt/wt % of sodium dodecylbenzene sulfonate and various amounts of poly(ethylene oxide) resins in deionized water. Comparative compositions (no surfactant) are prepared by dissolving various amounts of poly(ethylene oxide) resins in deionized water. The compositions are then sprayed through a Teejet 8001 flat fan nozzle (Spraying Systems Co.) at 40 psi using an air pressurized reservoir. The beam of a Malvern Mastersizer particle sizer (Malvern Instrument Company) is positioned 12.5 cm below the spray nozzle and the median diameters of the droplets are determined. The results are reported in Tables I, II and III.

As can be seen from the data in Tables I, II and III, the median droplet diameters produced by the aqueous spray compositions of the present invention are significantly greater than the median droplet diameters produced by the comparative compositions at the same concentration of poly(ethylene oxide) resin.

TABLE I

Median droplet diameter of various POLYOX ®N-12K[1] solutions

| POLYOX ®N-12K Concentration (wt/wt %) | Median Droplet Diameter (μm) | |
|---|---|---|
| | no NaDDBS | 0.15 wt/wt % NaDDBS[2] added |
| 0 | 142 | 127 |
| 0.0005 | 149 | 150 |
| 0.001 | 153 | 168 |
| 0.00125 | 155 | — |
| 0.0025 | 175 | 458 |
| 0.005 | 193 | 850 |
| 0.01 | 214 | >1,000 |
| 0.02 | 300 | >1,000 |
| 0.04 | 452 | — |

— = no evaluation
[1] A water-soluble poly(ethylene oxide) resin having an approximate molecular weight of $1 \times 10^6$ Daltons, manufactured by Union Carbide Corporation, Danbury, CT.
[2] sodium dodecylbenzene sulfonate

TABLE II

Median droplet diameter of various POLYOX ®N-60K[1] solutions

| POLYOX ®N-60K Concentration (wt/wt %) | Median Droplet Diameter (μm) | |
|---|---|---|
| | no NaDDBS | 0.15 wt/wt % NaDDBS[2] added |
| 0 | 142 | 127 |
| 0.0005 | — | 247 |
| 0.001 | 174 | 401 |
| 0.00125 | — | 552 |
| 0.0025 | 216 | >1,000 |
| 0.005 | 268 | — |
| 0.01 | 408 | — |
| 0.02 | 713 | — |

— = no evaluation
[1] A water-soluble poly(ethylene oxide) resin having an approximate molecular weight of $2 \times 10^6$ Daltons, manufactured by Union Carbide Corporation, Danbury, CT.
[2] sodium dodecylbenzene sulfonate

TABLE III

Median droplet diameter of various POLYOX ®Coagulant[1] solutions

| POLYOX ®Coagulant Concentration (wt/wt %) | Median Droplet Diameter (μm) | |
|---|---|---|
| | no NaDDBS | 0.15 wt/wt % NaDDBS[2] added |
| 0 | 142 | 127 |
| 0.0005 | 178 | 358 |
| 0.001 | — | 750 |
| 0.00125 | 228 | >1,000 |
| 0.0025 | 312 | >1,000 |
| 0.005 | 508 | — |
| 0.01 | >1,000 | — |

— = no evaluation
[1] A water-soluble poly(ethylene oxide) resin having an approximate molecular weight of $5 \times 10^6$ Daltons, manufactured by Union Carbide Corporation, Danbury, CT.
[2] sodium dodecylbenzene sulfonate

I claim:

1. An aqueous spray composition having a plurality of spray droplets with a median diameter, for applying about 0.001 to 50 wt/wt % of a pesticide, the improvement comprising about 0.001 to 1 wt/wt % of a water-soluble poly(ethylene oxide) having a molecular weight greater than about $5 \times 10^5$ Daltons, and at least about 0.05 wt/wt % of a surfactant selected from the group consisting of a sulfonated surfactant, a sulfated surfactant and mixtures thereof, provided that the surfactant has at least one straight or branched carbon chain containing at least nine carbon atoms, wherein, for a given spray apparatus, application, and conditions, and based on the water-soluble polymer and surfactant, the median diameter of the plurality of spray droplets is increased above that of an aqueous spray composition without said water-soluble polymer and surfactant.

2. The composition according to claim 1 wherein said poly(ethylene oxide) has a molecular weight of about $1 \times 10^6$ to $1 \times 10^7$ Daltons.

3. The composition according to claim 1 wherein said polymer is added at about 0.005 to 0.05 wt/wt %, and said surfactant is added at about 0.05 to 1 wt/wt %.

4. The composition according to claim 1 wherein said surfactant is selected from the group consisting of an α-olefin sulfonate, an alkylaryl sulfonic acid or salt, an alkyl sulfate, an α-olefin sulfate, an ethoxylated alcohol sulfate, an ethoxylated alkylphenol sulfate, and mixtures thereof.

5. The composition according to claim 4 wherein said α-olefin sulfonate is an α-($C_9$–$C_{18}$)olefin sulfonate, said alkylaryl sulfonic acid or salt is a $C_9$–$C_{18}$ alkylbenzene sulfonic acid or salt, said alkyl sulfate is a $C_9$–$C_{18}$alkylsulfate, said α-olefin sulfate is an a-$C_9$–$C_{18}$ olefin sulfate, said ethoxylated alcohol sulfate is an ethoxylated $C_9$–$C_{18}$alcohol sulfate, said ethoxylated alkylphenol sulfate is an ethoxylated $C_9$–$C_{18}$alkyphenol sulfate.

6. A method for increasing the median diameter of spray droplets and reducing the spray drift of an aqueous spray composition, for applying about 0.001 to 50 wt/wt % of a pesticide, the improvement to the method comprising adding to the aqueous spray composition about 0.001 to 1 wt/wt % of a water-soluble poly(ethylene oxide) having a molecular weight greater than about $5 \times 10^5$ Daltons, and at least about 0.05 wt/wt % of a surfactant selected from the group consisting of a sulfonated surfactant, a sulfated surfactant and mixtures thereof, provided that the surfactant has at least one straight or branched carbon chain containing at least nine carbon atoms, wherein, for a given spray apparatus, application, and conditions, and based on the water-soluble polymer and surfactant, the median diameter of the plurality of spray droplets is increased above that of an aqueous spray composition without said water-soluble polymer and surfactant.

7. The method according to claim 6 wherein said polymer is added at about 0.005 to 0.05 wt/wt %, and said surfactant is added at about 0.05 to 1 wt/wt %.

8. The method according to claim 6 wherein said sulfonated surfactant is an α-olefin sulfonate or an alkylaryl sulfonic acid or salt, and said sulfated surfactant is an alkyl sulfate, an α-olefin sulfate, an ethoxylated alcohol sulfate, an ethoxylated alcohol sulfate or an ethoxylated alkylphenol sulfate.

9. The method according to claim 8 wherein said α-olefin sulfonate is an α-($C_9$–$C_{18}$)olefin sulfate, said alkylaryl sulfonic acid or salt is a $C_9$–$C_{18}$alkylbenzene sulfonic acid or salt, said alkyl sulfate is a $C_9$–$C_{18}$alkyl sulfate, said α-olefin sulfate is an α-($C_9$–$C_{18}$)olefin sulfate, said ethoxylated alcohol sulfate is an ethoxylated $C_9$–$C_{18}$alcohol sulfate, and said ethoxylated alkylphenol sulfate is an ethoxylated $C_9$–$C_{18}$alkylphenol sulfate.

10. A method for increasing the median diameter of spray droplets and reducing the spray drift of an aqueous spray composition, for applying about 0.001 to 50 wt/wt % of a pesticide, the improvement to the method comprising adding to the aqueous spray composition about 0.001 to 1 wt/wt % of a water-soluble poly(ethylene oxide) having a molecular weight of about $1 \times 10^6$ to $1 \times 10^7$ Daltons, and at least about 0.05 wt/wt % of a surfactant selected from the group consisting of a sulfonated surfactant, a sulfated surfactant and mixtures thereof, provided that the surfactant has at least one straight or branched carbon chain containing at least nine carbon atoms, wherein, for a given spray apparatus, application, and conditions, and based on the water-soluble polymer and surfactant, the median diameter of the plurality of spray droplets is increased above that of an aqueous spray composition without said water-soluble polymer and surfactant.

* * * * *